United States Patent
Smith et al.

(10) Patent No.: US 6,623,419 B1
(45) Date of Patent: Sep. 23, 2003

(54) THERAPEUTIC BACK BELT AND RELATED METHOD OF MANUFACTURE

(75) Inventors: Mark C. Smith, Rockford, MI (US); Sandra K. Hopwood, Grand Rapids, MI (US); David P. Pearson, Thousand Oaks, CA (US)

(73) Assignee: Access Business Group International LLC, Ada, MI (US)

( * ) Notice: Subject to any disclaimer, the term of this patent is extended or adjusted under 35 U.S.C. 154(b) by 0 days.

(21) Appl. No.: 10/132,871

(22) Filed: Apr. 25, 2002

(51) Int. Cl.⁷ .............................. A71N 1/00; A61F 5/03
(52) U.S. Cl. .......................................... 600/15; 602/19
(58) Field of Search ....................... 600/9, 15; 602/19, 602/13, 2, 5; 128/845, 876, 118.1, 101.1, 106.1, 875, 96.1; 2/44, 338, 235, 236; 607/108; 482/106; 5/430; 528/61, 63, 54

(56) References Cited

U.S. PATENT DOCUMENTS

| | | | |
|---|---|---|---|
| 198,008 A | 12/1877 | Edard | |
| 3,921,620 A | 11/1975 | Nakayama | |
| 3,943,912 A | 3/1976 | Nakayama | |
| 4,022,189 A | 5/1977 | Boxer | |
| 4,033,054 A | 7/1977 | Fukuoka | |
| 4,135,503 A | * 1/1979 | Romano | 602/13 |
| 4,162,672 A | 7/1979 | Yazaki | |
| D261,936 S | 11/1981 | Sumiyasu | |
| 4,330,892 A | 5/1982 | Fukushima | |
| 4,391,270 A | 7/1983 | Uragami | |
| 4,480,596 A | 11/1984 | Shumiyashu | |
| 4,489,711 A | 12/1984 | Latzke | |
| 4,509,219 A | 4/1985 | Yagi | |
| 4,549,532 A | 10/1985 | Baermann | |
| 4,587,956 A | 5/1986 | Griffin et al. | |
| 4,592,358 A | 6/1986 | Westplate | |
| 4,798,194 A | 1/1989 | Amishima | |
| 4,886,063 A | 12/1989 | Crews | |
| 4,921,560 A | 5/1990 | Yamaguchi | |
| 5,017,185 A | 5/1991 | Baermann | |
| 5,045,050 A | 9/1991 | Liboff et al. | |
| 5,137,507 A | 8/1992 | Park | |
| 5,179,942 A | * 1/1993 | Drulias et al. | 128/101.1 |

(List continued on next page.)

FOREIGN PATENT DOCUMENTS

| | | |
|---|---|---|
| DE | 2733982 | 2/1979 |
| EP | 100050 | 2/1984 |
| EP | 334141 | 9/1989 |

OTHER PUBLICATIONS

Lin, James C. et al, *Geophysical Variables and Behavior: XXVII. Magnetic Necklace: Its Therapeutic Effectiveness on Neck and Shoulder Pain: 2. Psychological Assessment*, Psychological Reports (Apr. 1985).

*Primary Examiner*—Eric F. Winakur
*Assistant Examiner*—Nikita R Veniaminov
(74) *Attorney, Agent, or Firm*—Warner Norcross & Judd LLP (57) ABSTRACT

A back belt including magnets, and a thermally active gel material to provide magnetic and thermal induced lower back pain relief. The magnets are arranged in multiple quadrapolar pods, which are secured to a contour-conforming, resilient support web. Preferably, an interior sheet sandwiches the pods and gel material between it and an exterior sheet in a cross-shaped array within the support web. In a more preferred embodiment, the belt includes a fastening strap that neatly secures excess belt by wrapping around the excess belt and drawing that excess against the remainder of the belt. In a preferred process of manufacturing the back belt, multiple quadrapolar magnet pods and the gel material are secured to a support web. Belt straps are secured to the support web. More preferably, a fastening strap is secured to at least one of the belt straps.

21 Claims, 8 Drawing Sheets

U.S. PATENT DOCUMENTS

| | | | |
|---|---|---|---|
| 5,214,404 A | | 5/1993 | Yamaguchi et al. |
| 5,232,424 A | * | 8/1993 | Pearson et al. ............. 482/106 |
| 5,232,433 A | | 8/1993 | Kotsuka |
| 5,277,692 A | | 1/1994 | Ardizzone |
| 5,304,111 A | | 4/1994 | Mitsuno et al. |
| 5,312,321 A | | 5/1994 | Holcomb |
| 5,389,061 A | | 2/1995 | Nor |
| 5,389,981 A | | 2/1995 | Riach, Jr. |
| 5,426,925 A | | 6/1995 | Smargiassi |
| 5,445,601 A | * | 8/1995 | Harlow ........................ 602/19 |
| 5,450,858 A | | 9/1995 | Zablotsky et al. |
| 5,456,701 A | | 10/1995 | Stout |
| 5,478,303 A | | 12/1995 | Foley-Nolan et al. |
| 5,484,366 A | | 1/1996 | Wilkinson |
| 5,499,965 A | * | 3/1996 | Sanchez ..................... 602/19 |
| 5,514,072 A | | 5/1996 | Ardizzone |
| 5,538,495 A | | 7/1996 | Ardizzone |
| D375,186 S | | 11/1996 | Kim |
| 5,621,369 A | | 4/1997 | Gardner et al. |
| 5,642,739 A | | 7/1997 | Fareed |
| 5,665,057 A | | 9/1997 | Murphy |
| 5,707,333 A | * | 1/1998 | Bakst ........................... 600/9 |
| 5,720,046 A | | 2/1998 | Lopez et al. |
| 5,738,624 A | | 4/1998 | Zablotsky et al. |
| 5,782,743 A | * | 7/1998 | Russell ......................... 600/9 |
| 5,792,176 A | | 8/1998 | Chang |
| 5,807,233 A | | 9/1998 | Sakuma et al. |
| 5,813,971 A | | 9/1998 | Broderick |
| D399,567 S | | 10/1998 | Affholter |
| 5,827,170 A | | 10/1998 | Gebran |
| 5,843,008 A | * | 12/1998 | Gerhard ........................ 602/5 |
| 5,887,437 A | | 3/1999 | Maxim |
| 5,950,239 A | | 9/1999 | Lopez |
| 5,971,947 A | | 10/1999 | McNally et al. |
| 5,984,855 A | | 11/1999 | DiNapoli |
| 5,993,375 A | | 11/1999 | Engel |
| 6,006,363 A | | 12/1999 | Karlin |
| 6,017,606 A | | 1/2000 | Sage et al. |
| 6,019,782 A | | 2/2000 | Davis et al. |
| 6,024,761 A | | 2/2000 | Barone et al. |
| 6,048,303 A | | 4/2000 | Porter |
| 6,048,326 A | | 4/2000 | Davis et al. |
| 6,074,413 A | | 6/2000 | Davis et al. |
| 6,099,555 A | | 8/2000 | Sabin |
| 6,123,717 A | | 9/2000 | Davis et al. |
| 6,126,588 A | | 10/2000 | Flamant et al. |
| 6,127,505 A | * | 10/2000 | Slagel ........................ 528/61 |
| 6,129,659 A | | 10/2000 | Wilk |
| 6,132,454 A | | 10/2000 | Fellows |
| 6,132,455 A | | 10/2000 | Shang |
| 6,139,486 A | | 10/2000 | Matuszewski et al. |
| 6,146,324 A | | 11/2000 | Engel |
| 6,187,031 B1 | | 2/2001 | Douglas |

* cited by examiner

THERAPEUTIC BACK BELT AND RELATED METHOD OF MANUFACTURE

BACKGROUND

The present invention relates to a therapeutic back belt, and more particularly to a back belt including magnets that address pain originating in the lower back.

The application of magnetic fields to areas of the human body experiencing pain has become a widely accepted method of treating that pain. Such treatment is sometimes preferred over other conventional methods, such as surgery or administration of drugs, because, among other reasons, it is less invasive. It is believed that when a magnetic field is applied to an area of localized pain, it blocks chemical channels in nerve cells in the area of pain. As a result, the generation of pain impulses from the nerve cells, and subsequent transmission along the nerve cell fibers to the brain is reduced, thereby relieving the pain.

Magnetic therapy has proven to be particularly helpful in reducing lower back pain, that is, pain originating in the sacral or lumbar regions of the back. One device used to provide magnetic therapy to the lower back is disclosed in U.S. Pat. No. 4,480,596 to Shumiyashu. In Shumiyashu, an array of magnets is positioned on a belt so that all the magnets exert either a positive or a negative magnetic field toward the lower back when the belt is worn around the waist of a user. The magnets are maintained in fixed positions relative to one another with a rigid plastic support sheet so that they do not attract one another and collapse the belt into a ball.

Although prior art magnetic back belts provide therapeutic magnetic fields to treat lower back pain, they suffer from several shortcomings. First, because the magnetic array covers the entire lower back region, the belts are singular in function, providing only magnetic therapeutic relief for lower back pain. Second, because all the magnets in the array are positioned to exert only either a positive or a negative field toward the lower back, it is believed that treated nerve cells in the lower back become accustomed to the same, singular field and reinitiate transmission of pain signals from the nerve cells over time. Further, the rigid plate, which prevents mutual magnetic attraction or repulsion of the magnets relative to one another, makes conventional magnetic belts uncomfortable to wear, restricts movement of a wearer and applies uneven pressure across the lower back. Finally, the adjustment straps of typical belts are designed to be of a length long enough to fit around the waist of the largest dimensioned users. Thus, small-dimensioned users must either cut-off excess strap material or stuff it under the other adjustment strap so that it does not hang loosely. By cutting an end of the belt off, it cannot be transferred to a larger user. Moreover, stuffing one strap under the other usually creates a mass of adjustment straps that is difficult to conceal under clothing and can be uncomfortable. In some cases, manufacturers produce belts of several sizes to accommodate a range of different waist sizes, however, this complicates manufacturing and distribution.

SUMMARY OF THE INVENTION

The aforementioned problems are overcome in the present invention wherein a back belt includes a contour-forming support web having multiple magnetic bodies and a material that provides both magnetic pain relief, thermal comfort, and muscle relaxation to the lower back.

In a preferred embodiment of the invention, magnetic bodies are disposed on an elastic, contour-forming support web, having adjustment straps attached thereto. A gel region is also included in the web.

In a more preferred embodiment of the invention, the magnetic bodies are disposed in a group, or "pod," of four magnets, each having two opposing (positive and negative) poles. Two positive poles of two magnets and two negative poles of two of the other magnets are disposed in a single plane in a diagonally alternating configuration.

In a more preferred embodiment, the pods are disposed in a cross-shape, with a column of pods aligned with the vertebrae of a user and a row of pods perpendicular to the column and configured to align across the lower lumbar-sacral region. The support web may include an opening at the intersection of the row and column of magnetic pods.

In a second aspect of the invention, the belt includes a fastening strap to neatly secure any excess portion of the belt to the remainder of the belt when the belt is positioned around a user's waist.

The back belt of the present invention provides many benefits. First, it is multi-functional, providing both magnetic fields and thermal properties to relieve and/or reduce pain originating in the lower back. Second, the flexible support web allows the magnetic pods to conform closely to the contours of the lower back, thereby bringing the magnetic fields closer to the nerves therein for pain treatment. Moreover, with the body conforming fit, the belt does not ride-up a user's back, provides the user with a greater range of motion and significantly reduces the likelihood of pinching skin between the web and the belt. Third, with the quadrapolar magnetic pods, both positive and negative magnetic fields are applied to the nerves in the lower back to provide alternating magnetic forces to those nerves. Finally, the fastening strap of the present invention eliminates unsightly loose or bunched belt ends.

These and other objects, advantages and features of the invention will be more readily understood and appreciated by reference to the detailed description of the preferred embodiments and the drawings.

DETAILED DESCRIPTION OF THE INVENTION

Figure 1:
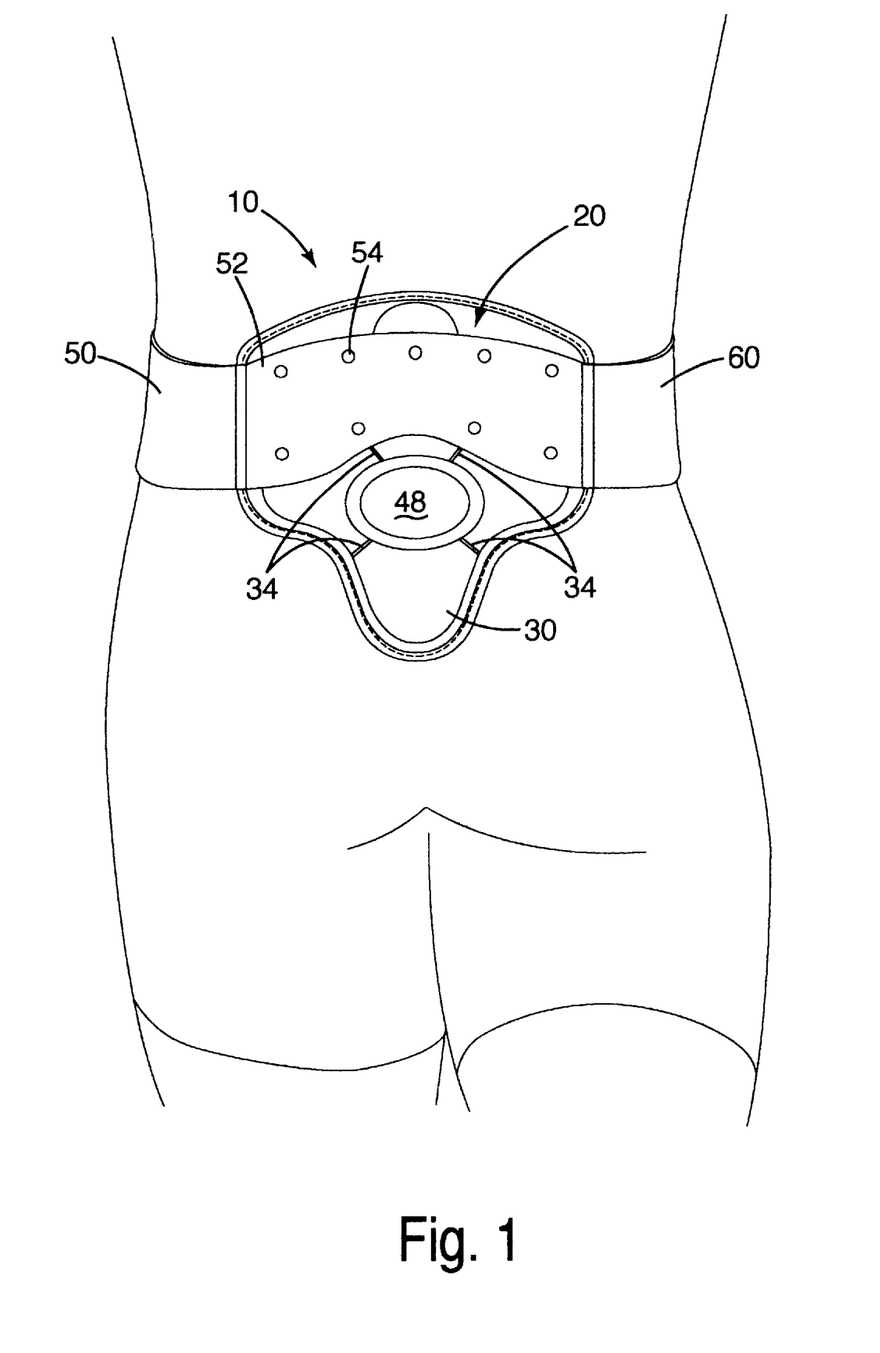
FIG. 1 is a perspective view of the back belt of the present invention disposed around the waist of a user.
Figure 2:
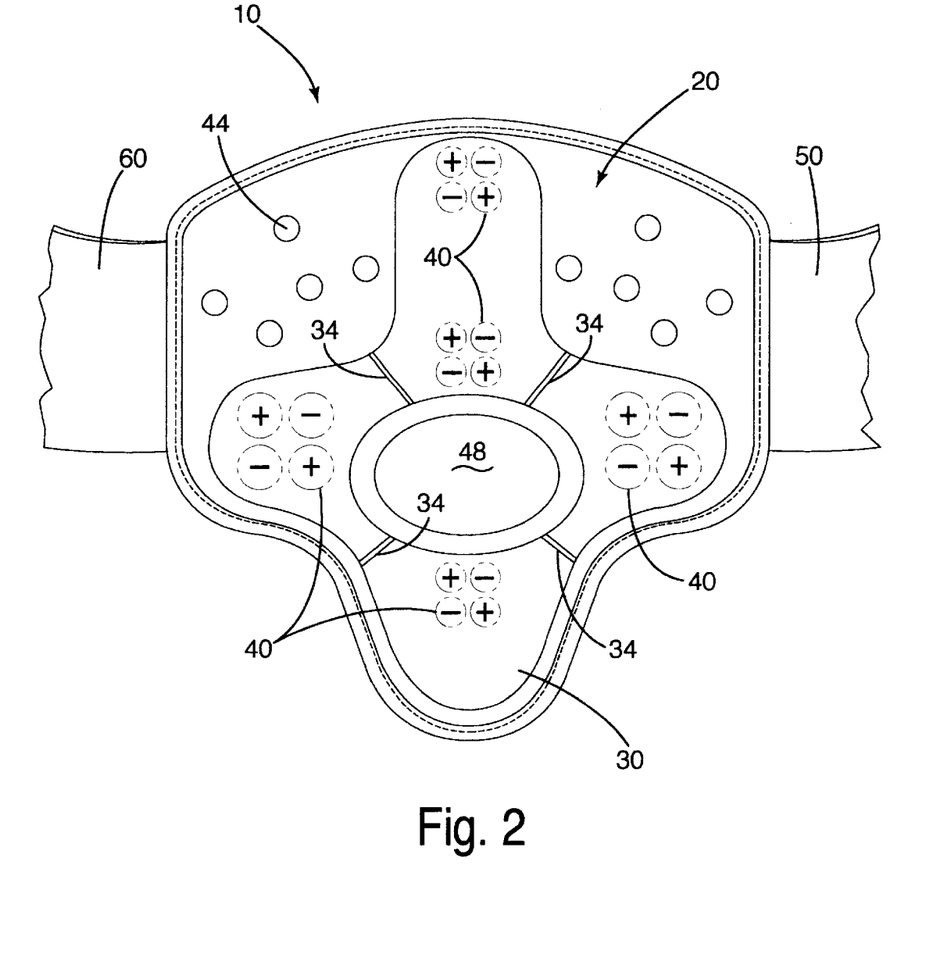
FIG. 2 is an interior view of the back belt laid open.

A preferred embodiment of the back belt 10 of the present invention is shown in FIGS. 1 and 2 and generally includes support web 20, and adjustment straps 50 and 60. The support web 20 further includes gel region 30, magnetic bodies, or "pods" 40, and defines locating aperture 48. In use, the adjustment straps are wrapped around the waist of a user so that the support web 20 is positioned over the lumbar-sacral region of the user's back.

Figure 7:
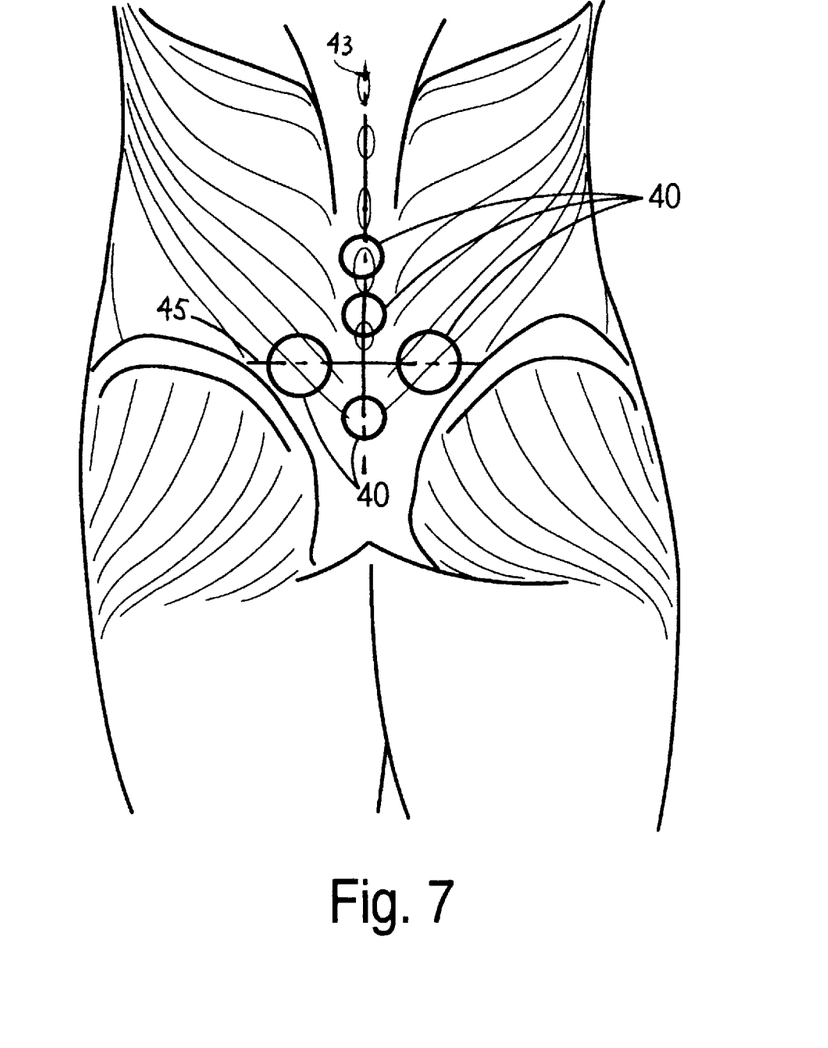
FIG. 7 is a plan view of magnets of the back belt positioned over a wearer's back muscles.

With reference to FIGS. 2–5, the support web will now be described. The magnetic bodies or pods 40 disposed in the support web 20 are configured in a somewhat cross shape, with a column of pods positioned to align along the spine of a wearer. A row of pods is disposed perpendicular to the column of pods and positioned to align substantially across the lower sacral muscles. FIG. 7 shows by outline, the preferred location of the magnet pods 40 on the body. The column 43 of magnet pods 40 is parallel to and aligned with the spine and the row 45 of magnet pods 40 is substantially perpendicular to the column and disposed over the lower sacral muscles. With the pods 40 arranged in this configuration, it is believed that the magnetic fields generated by the pods 40 may be positioned over the spine to relieve lower back pain. Preferably, each of the pods in the column 43 along the spine exert about 1000–1200 Gauss in the region of the back adjacent to the pod. Preferably, each of the magnetic pods in the row 45 perpendicular to the column disposed substantially over the lower sacral regions exert about 1300–1500 Gauss in the region of the back adjacent to the pod. Over the entire region of the back that the support web is positioned over, the Gauss exerted on that region is preferably 100–5000 Gauss, more preferably 1000–3000, even more preferably 1500–2000 and most preferably about 1500 Gauss.

Figure 6:
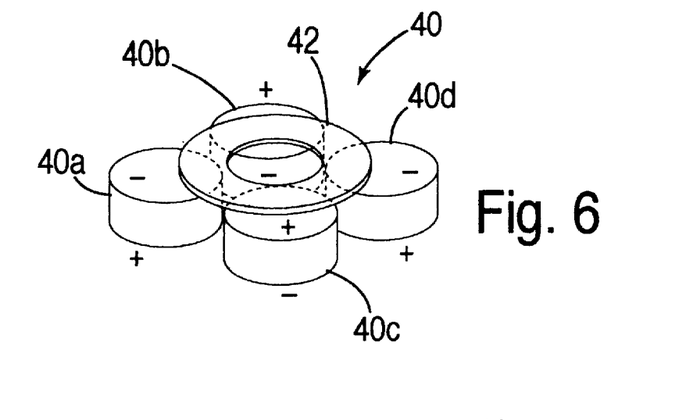
FIG. 6 is a perspective view of a magnet pod of the back belt.

Preferably, each pod 40 includes magnets configured as shown in FIG. 6 with four polar magnetic bodies 40a–40d. Preferably, the magnetic bodies are disposed in a quadropolar group, having two positive circular magnetic poles and two negative circular poles of approximately equal strength lying substantially in a first plane. The magnetic bodies are orientated such that the two positive poles and two negative poles lying in the first plane define the four vertices of a rectangular shape with the two positive poles defining two diagonal vertices and the two negative poles defining opposite vertices of the rectangular shape. The configuration of the four magnetic bodies is preferably constructed in accordance with the teachings of U.S. Pat. No. 5,312,321 to Holcomb, which is hereby incorporated by reference.

Figure 3:
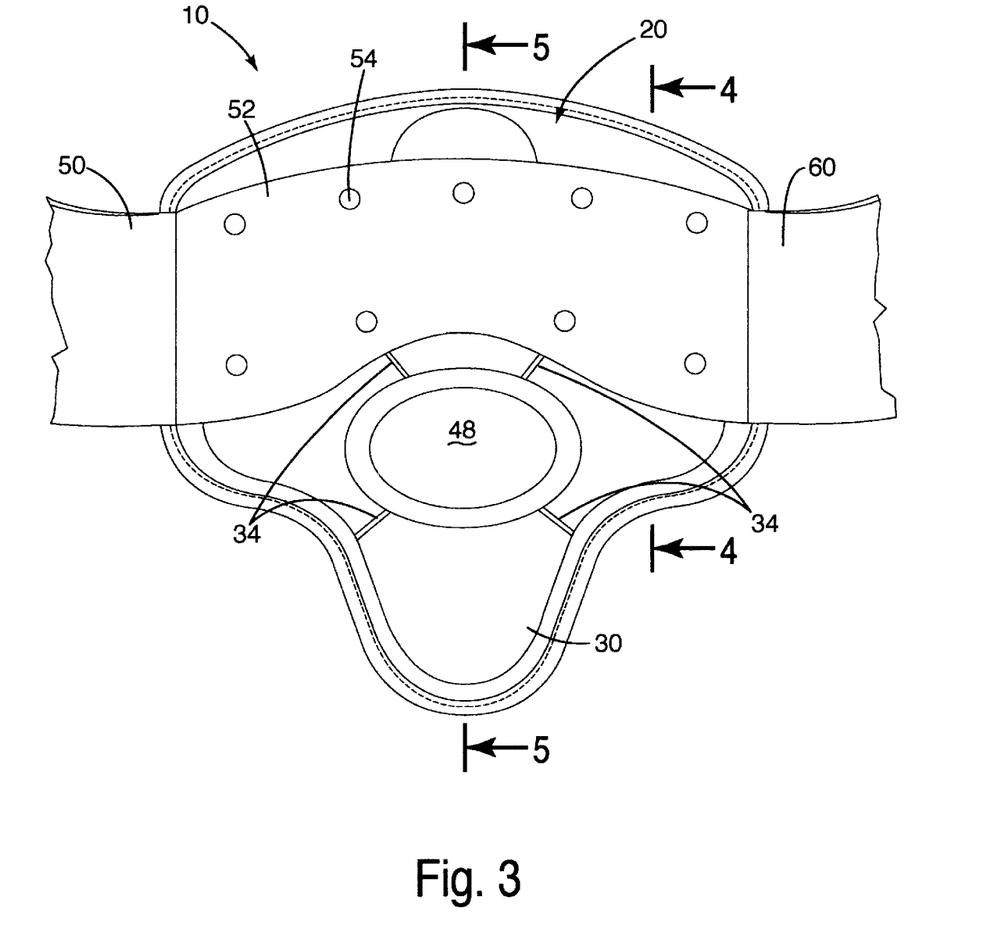
FIG. 3 is an exterior view of the back belt laid open.
Figure 4:
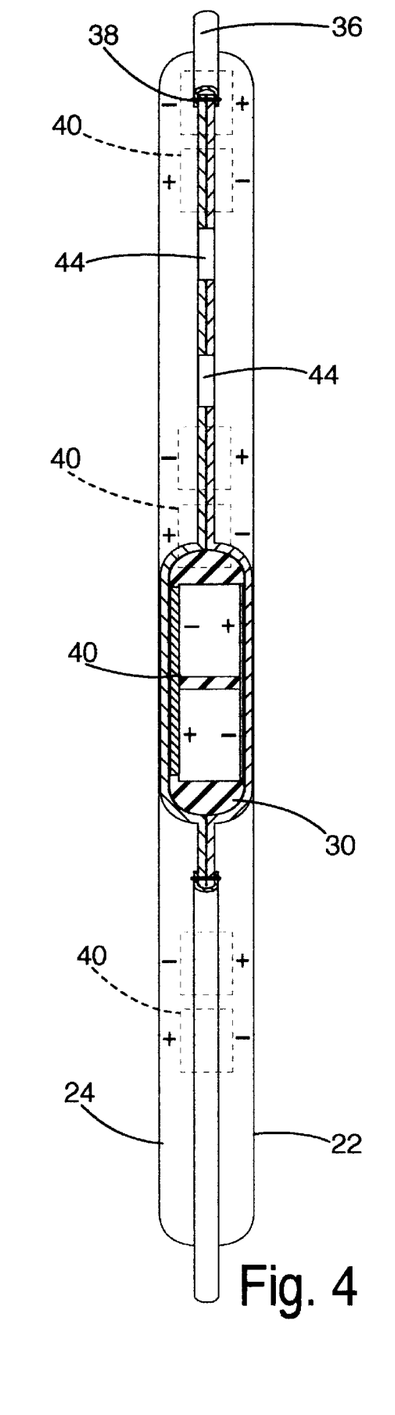
FIG. 4 is a sectional view of the back belt taken along line 4—4 of the FIG. 3.
Figure 5:
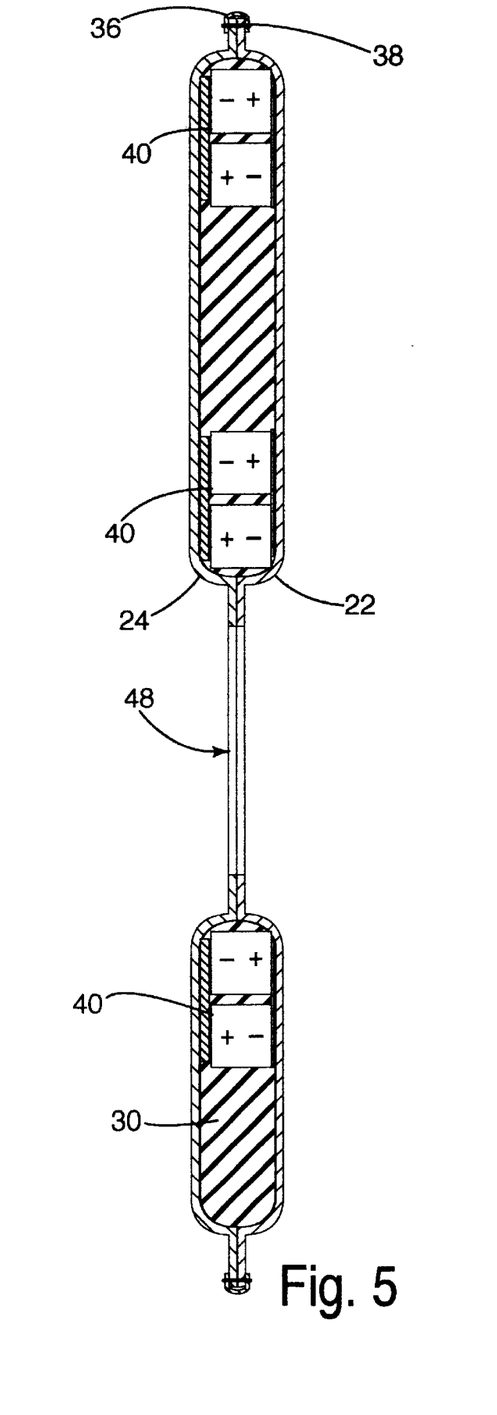
FIG. 5 is a sectional view taken along line 5—5 of FIG. 3.

Optionally, the magnets are secured to washer 42 which is configured to add rigidity and hold the quadrapolar group of magnets in position during use. Preferably, the washer is positioned opposite of the body to channel the magnetic field to the body. With further reference to FIGS. 2–5, the gel region will now be described. As shown in FIGS. 2, 4 and 5, the gel region is substantially configured in a cross-like shape substantially corresponding with the column and rows of pods 40. The gel region 30 is constructed of a conventional gel and/or gel-like material, such as gel foam, which is commonly known as a gel, or polymer, which, depending on the type of polymer, may or may not be known as a gel. The type of gel material used may be that commercially available for heat or ice compresses or packs. This material is preferably refreezeable and capable of being heated prior to use. Optionally, the gel region may be compartmentalized with separating elements 34. If one of the compartments ruptures, the other compartments are still functional.

FIGS. 4 and 5 show the layered construction of the support web 20. That web is generally constructed of inner sheet 22 and outer sheet 24. Both sheets are preferably stretchable, resilient and/or substantially elastic material, such as the material sold under the trade name Lycra®. With an elastic sheet construction, the support web conforms to the contours of a user's back when the belt 10 is worn about a user's waist. The sheets as described may be substantially elastic to enhance the support web's conformity to the contour of a user's back when the belt is worn around the user's waist.

The sheets are secured to one another around the gel region 30, which is preferably substantially filled with the gel as described above. The sheets may be secured with a suitable adhesive, sewn or fused together in a welding or heating process. At the edges of the support web 20, a trim piece or border 36 may be secured over the free edges of the sheets 22 and 24 to produce a finished appearance and prevent fraying of the free edges. This trim piece 36 may be secured to the sheets with stitching 38 through the trim piece and through the sheets. Optionally, the terminal edges may be stitched to one another without a trim piece. Alternatively, one of the edges, for example, the edge of the outer sheet 24 may extend past the edge of the inner sheet 22 and double over onto the inner sheet. The two sheets may then be stitched together in this doubled over region. This will conceal the joint. The edge of sheets may also be left unsecured.

Inner 22 and outer 24 sheets also define a locating aperture 48, which is generally positioned at the intersection of the column and row of magnetic pods 40. The inner 22 and outer 24 sheets preferably are sealed together along the edges defining the aperture. The locating aperture assists the user in positioning the column over the spine and row over the lower sacral muscles. For example, the user may put a finger through the aperture and feel the spine as she places the belt 10 about her waist.

The inner 22 and outer 24 sheets may further define ventilating apertures 44 to ventilate a user's back when the belt is worn. The positioning and number of the ventilating apertures may be selected as desired to maximize ventilation efficiency.

With reference to FIGS. 1 and 8–11, the adjusting straps 50 and 60 of the preferred embodiment will now be described. The adjusting straps are preferably constructed of an elastic material, for example, a woven elastic material, or materials available under the trade names Lycra® and Spandex®. Preferably one end of each of the straps is secured to the support web 20 with stitching, adhesive or other fastener. Alternatively, the adjustment straps 50 and 60 may be a single strap that crosses and is secured to the support web 20. Optionally, a reinforcement strap 52 may further connect the adjustment straps across the support web 20 to assist in pulling the support web close to the spinal and lumbar sacral muscles. This reinforcement strap is preferably constructed of a resilient material, such as Lycra®, and includes ventilation apertures 54 to enhance ventilation of the user's back under the support web.

Figure 8:
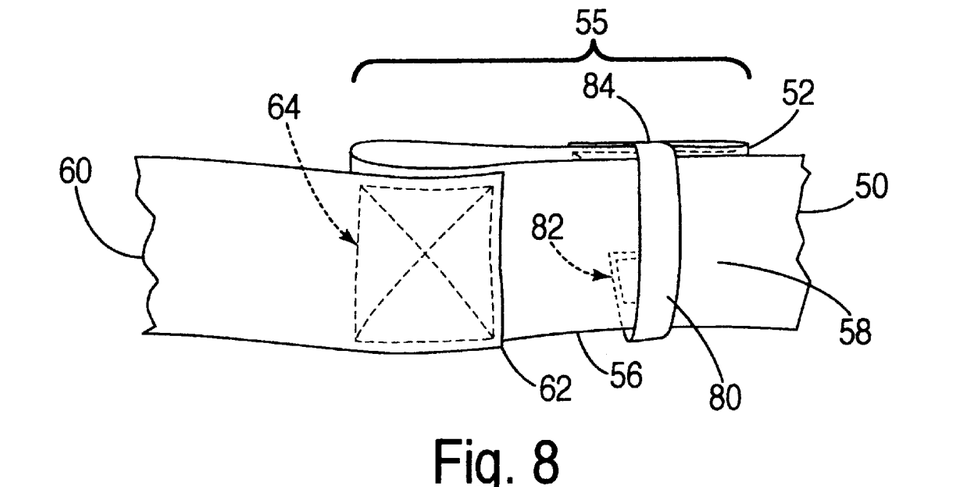
FIG. 8 is a front perspective view of a fastening strap of the back belt.
Figure 9:
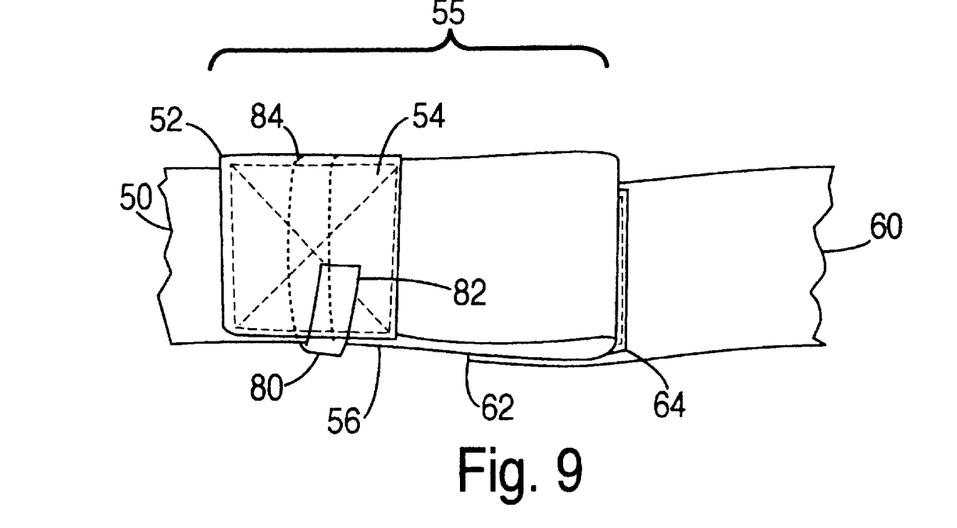
FIG. 9 is a rear perspective view of the fastening strap.

In a preferred embodiment shown in FIGS. 8 and 9, the straps terminate at ends 52 and 62. One hook-and-loop type fastener is secured to front face 58 of strap 50 and the other corresponding hook-and-loop type fastener is secured to a patch 64 on the rear side of strap 60. Patch 64 is of a sufficient size to form a strong connection with the front face 58 of strap 50 when the belt is worn. A user may perform adjustments to make the belt fit more or less tightly by attaching the hook-and-loop type fastener 64 at different locations along the length of the strap 50.

Figure 10:
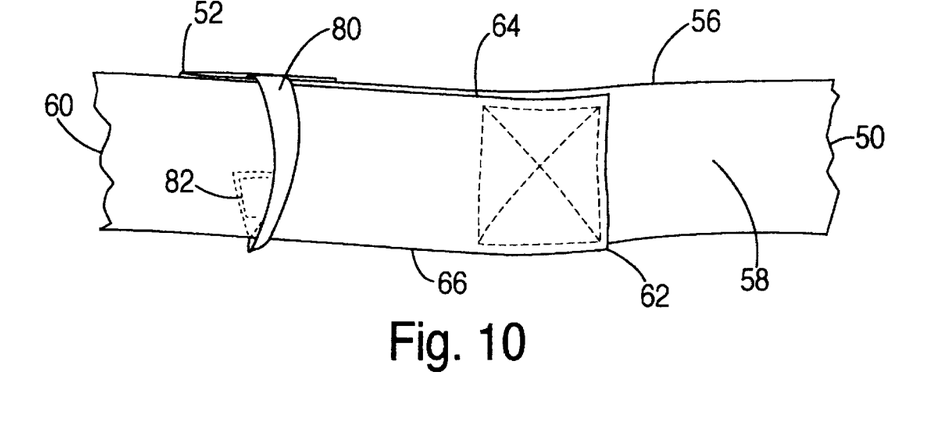
FIG. 10 is a front perspective view of a fastening strap in an alternative configuration.
Figure 11:
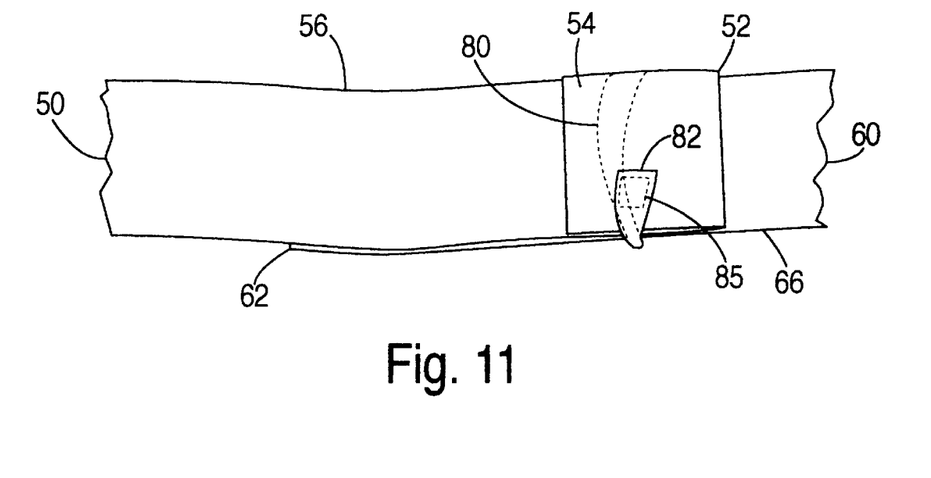
FIG. 11 is a second rear perspective view of the fastening strap in the alternative configuration.

As shown in FIGS. 8 and 9, the strap 50 may be doubled over on itself or on main body 56 of the strap 50, if the straps are too long and form an excess portion 55. This situation is desirable if the straps are greater in length than the distance around a user's waist. Alternatively, as shown in FIGS. 10 and 11, the straps may be overlapped on one another. For example, end 52 overlaps main body 66 of the strap 60 and end 62 overlaps main body 56 of strap 50. The hook-and-loop type fastener of patch 64 secures end 62 to the face 58 of the main body 56.

In the preferred embodiment, one of the adjusting straps 50 and 60 includes a fastening strap 80, preferably at a free end 52 or 62. A first end of the fastening strap 84 is secured to the strap 50, preferably adjacent its free end 52. The fastening strap 80 may be made of a resilient material such as nylon webbing or stretchable material of a sufficient length so that the free end 82 may be wrapped substantially around the main body 56 of the strap 50 and onto the opposite side, along the excess portion 55 if such an excess portion exists. The end portion 82 preferably includes a hook-and-loop type fastener complimentary to the hook-and-loop type fastener on the face 58 to allow the end portion 82 to be secured to the excess portion in region 54 or near the end 52. This fastening strap feature 80 allows excess straps to be effectively and neatly stored away to prevent unsightly and uncomfortable bunched portions of the strap. It also makes it unnecessary to cut off the excess strap end if the belt is worn by a user with a small waist, that is, with measurements less than the length of the straps 50 and 60.

As shown in FIGS. 10 and 11, the same fastening strap 80 may be used to secure straps 50 and 60 to one another by wrapping the fastening strap 80 around the adjusting strap 60 and twisting the end 82 so that the hook-and-loop type fastener contacts the opposing hook-and-loop type fastener on the opposing fastener member 54 adjacent the end 52. Optionally, the end of the fastening strap 80 may be outfitted with an opposing hook-and-loop type fastener 85 on the opposite side of the end so that the fastening strap 80 need not be twisted when disposed around the adjusting strap 60. For example, in FIG. 11 the fastening strap 80 would not be twisted, and the hook-and-loop type fastener 85 would be directly fastened to the hook-and-loop fastening member 54.

Figure 12:
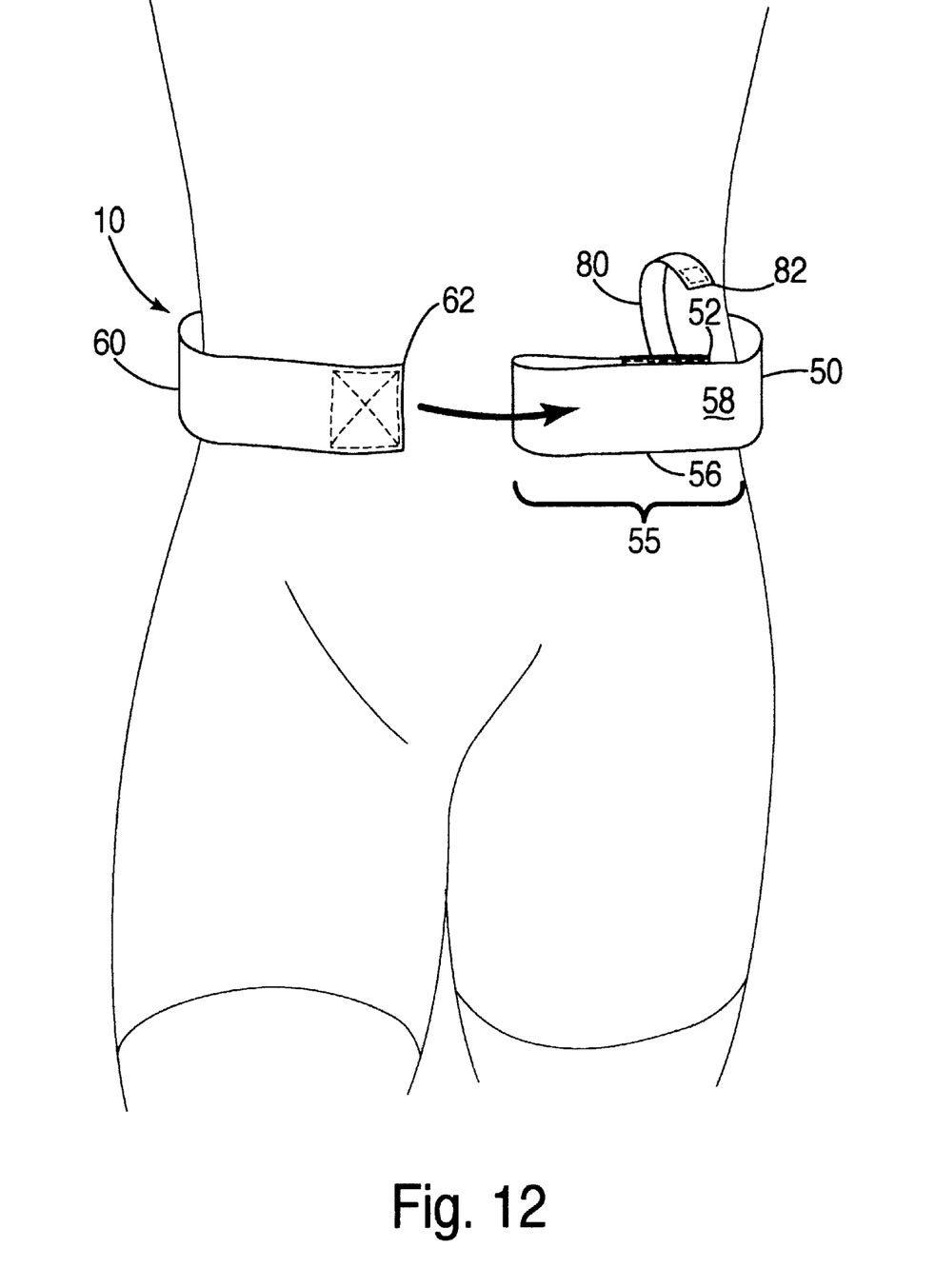
FIG. 12 is a front view of the fastening strap in operation.

With reference to FIG. 12, the operation of the belt will now be described. A user may position the belt around the user's waist as shown, with the adjusting straps 50 and 60 positioned so that ends 52 and 62 are generally in front of the user's torso. If the belt is too long, so that the end 52 does not marginally overlap the other end 62, the excess portion 55 of the belt 50 may be doubled over on the main body 56 of the strap 50. Fastening strap 80 is then wrapped substantially around the adjusting strap 50 along the main body so that the free end 82 faces the front face of the fastening strap (concealed on the excess portion and facing the user's body). The hook-and-loop fastener on the end of the strap 82 is then engaged against the opposing hook-and-loop type fastener on the concealed face 58 of the adjusting strap to secure the excess portion 55 to the main body of the belt 56. The end 62 of the belt 60 is then positioned over the face 58 of the adjusting strap 50 and secured thereto, thereby securing the belt 10 around the waist of the user and neatly storing away the excess portion 55.

The above descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular.

The embodiments of the invention in which an exclusive property or privilege is claimed are defined as follows:

1. A therapeutic back belt comprising:
   a belt having a first end and a second end configured to encircle a user's waist, said belt having a first means for fastening and a complementary means for fastening, said complementary means configured to engage said first means whereby the belt can be fastened to form a closed-loop belt,
   an elastic lumbar support member secured to said belt, said lumber support member including a gel region;
   a plurality of magnetic bodies disposed substantially within said gel region; and
   a fastening strap including a secured portion and a free end, said secured portion fixedly secured to said first end, said free end including a touch fastening element, said fastening strap wrapping substantially and transversely over said second end, said touch fastening element releasably securing the free end to at least one of the fastening strap, said first end, and said second end, wherein said first end is secured against said closed-loop belt.

2. The therapeutic back belt of claim 1 wherein each of said magnetic bodies in said plurality of magnetic bodies includes a quadrapolar group of four magnetic bodies having two positive circular magnetic poles and two negative circular magnetic poles of approximately equal strength and lying substantially in a first plane, said magnetic bodies being disposed in an orientation such that said two positive poles and said two negative poles lying in said first plane define the four vertices of a rectangular shape with said two positive poles defining two diagonal vertices and said two negative poles defining opposite vertices of said rectangular shape.

3. The therapeutic back belt of claim 1 wherein said gel region includes a thermal material.

4. The therapeutic back belt of claim 1 wherein said gel region is configured in the shape of a first cross.

5. A therapeutic back belt comprising:
   a belt having a first end and a second end configured to encircle a user's waist, said belt having a first means for fastening and a complementary means for fastening said complementary means configured to engage said first means whereby the belt can be fastened to form a closed-loop belt,
   an elastic lumbar support member secured to said belt, said lumber support member including a gel region;
   a plurality of magnetic bodies disposed substantially within said gel region;
   a fastening strap including a secured portion and a free end, said secured portion secured to at least one of said first end and said second end, said free end including a fastener, said fastening strap wrapping substantially around the other of said first end and said second end, said fastener releasably securing the free end to at least one of the fastening straps and the other of said first end and said second end wherein the other of said first end and said second end is secured against said closed-loop belt and wherein said gel region is configured in the shape of a first cross; and
   wherein said magnetic bodies form a column and a row in the shape of a second cross substantially corresponding to said first cross and including an intersection.

6. The therapeutic back belt of claim 5 wherein said elastic lumbar support member defines an opening at said intersection, said opening adapted to assist a user in positioning the column of magnetic bodies in alignment with the user's spine.

7. The therapeutic back belt of claim 6 wherein said fastening means is a hook-and-loop fastener.

8. A back belt comprising:
   a belt portion including first and second ends, and means to connect said first and second ends to one another to secure the belt around the waist of a user;
   a flexible support web attached to said belt including an elastic interior sheet and an elastic exterior sheet;
   a plurality of quadrapolar magnet pods sandwiched between said elastic interior sheet and said elastic exterior sheet, said plurality of quadrapolar magnet pods adhered to at least one of said interior and exterior sheets, said pods held in fixed relation to the support web; and
   a gel pad secured to said support web substantially surrounding each of said plurality of quadrapolar magnet pods.

9. The back belt of claim 8 comprising a resilient secondary support belt overlaying said exterior sheet and secured to at least one of said belt portion and said flexible support web.

10. The back belt of claim 8 wherein said plurality of quadrapolar magnet pods are configured in a first row and a second row, the first and second rows meeting at an intersection.

11. The back belt of claim 10 wherein said flexible support web defines an opening that corresponds to said intersection.

12. The back belt of claim 8 wherein said belt portion includes a main body adjacent said second end, wherein said second end is adapted to double over said main body and form an excess portion, said belt portion including a fastening strap secured to said second end, said fastening strap including a fastening end and being of a length sufficient to wrap around said main body and secure said second end to said main body.

13. The back belt of claim 8 wherein said first and second ends overlap one another to form an excess portion when the belt portion is disposed around the waist of a user, and comprising a fastening strap secured to said belt portion and adapted to wrap around said excess portion and secure said excess portion to at least one of said first and second ends.

14. A back belt for relieving lower back pain comprising:
   a support web including at least one of a thermal treatment material and a plurality of magnetic devices;
   a belt secured to said support web including a first portion having one of a hook-and-loop fastener and terminating at a first belt end, a second portion having the other of the hook-and-loop fastener and terminating at a second belt end, said second belt end adapted to fold over the second portion to form an excess portion; and
   a fastening strap including a first strap end and a second strap end, said first strap end fixedly secured to at least one of said first belt end and said second belt end, said second strap end including a touch fastening element that releasably fastens the fastening strap to at least one of the hook-and-loop fasteners, said fastening strap wrapping substantially and transversely over said second portion to releasably secure said second end to the belt and store said excess portion.

15. The back belt of claim 14 wherein said magnetic devices each include four cylindrical magnets having two positive circular magnetic poles and two negative circular magnetic poles of approximately equal strength and lying substantially in a first plane, said magnetic bodies being disposed in an orientation such that said two positive poles and said two negative poles lying in said first plane define the four vertices of a rectangular shape with said two positive poles defining two diagonal vertices and said two negative poles defining opposite vertices of said rectangular shape.

16. The back belt of claim 14 wherein said support web includes an flexible interior sheet and a flexible exterior sheet secured to one another to sandwich said at least one of said thermal treatment material and plurality of magnetic devices therebetween.

17. The back belt of claim 16 comprising a secondary support strap extending substantially across said support web.

18. A method for manufacturing a back pain relieving device comprising:
   providing an elastic base sheet designed to be positioned against a person's lower back, said base sheet including a longitudinal axis configured to align parallel to lumbar muscles along the persons' spine and at least one transverse axis substantially perpendicular to said longitudinal axis;
   securing a first plurality of quadrapolar magnetic devices to said base sheet along the longitudinal axis of the base sheet;
   securing a second plurality of quadrapolar magnetic devices to said base sheet along said transverse axis; and
   attaching a gel material to said elastic base sheet wherein said gel material substantially surrounds at least one of said first and second plurality of quadrapolar magnetic devices.

19. The method of claim 18 comprising securing the elastic base sheet to an elongate belt including fastening means for securing the belt circumferentially about a person's waist.

20. The method of claim 19 comprising securing a fastening strap to the elongate belt, wherein the elongate belt includes a first end and a second end, the second end adapted to fold over on the elongate belt to form an excess portion when the belt is longer than a distance around a wearer's waist, the fastening strap of a length sufficient to wrap around at least one of the second end and the belt and secure the excess portion to the belt.

21. The method of claim 19 comprising securing a fastening strap to the elongate belt, wherein the elongate belt includes a first end and a second end adapted to overlap said first end and form an excess portion when the belt is longer than the distance around a wearer's waist, the belt including a fastening strap of a length sufficient to wrap around at least one of the second end and the belt and secure the excess portion to the belt.

* * * * *